US012462922B2

(12) United States Patent
Wiggermann et al.

(10) Patent No.: US 12,462,922 B2
(45) Date of Patent: Nov. 4, 2025

(54) MEDICAL LINE DETECTION AND MONITORING USING VIDEO

(71) Applicant: Hill-Rom Services, Inc., Batesville, IN (US)

(72) Inventors: Neal Wiggermann, Batesville, IN (US); Nicholas A. Mann, Cincinnati, OH (US); Gene J. Wolfe, Pittsford, NY (US); Robert M. Zerhusen, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 419 days.

(21) Appl. No.: 18/156,506

(22) Filed: Jan. 19, 2023

(65) Prior Publication Data

US 2023/0268058 A1 Aug. 24, 2023

Related U.S. Application Data

(60) Provisional application No. 63/312,410, filed on Feb. 22, 2022.

(51) Int. Cl.
*G16H 30/40* (2018.01)
*G16H 40/60* (2018.01)

(52) U.S. Cl.
CPC ............. *G16H 30/40* (2018.01); *G16H 40/60* (2018.01); *G06T 2207/10028* (2013.01)

(58) Field of Classification Search
USPC ........................................................ 382/128
See application file for complete search history.

(56) References Cited

U.S. PATENT DOCUMENTS

| | | | |
|---|---|---|---|
| 9,308,323 B2 | 4/2016 | Adams | |
| 10,639,416 B2 | 5/2020 | Utz | |
| 11,033,670 B2 | 6/2021 | Scarpaci et al. | |
| 2006/0052766 A1 | 3/2006 | Patel | |
| 2013/0208497 A1 | 8/2013 | Provost et al. | |
| 2019/0217006 A1 | 7/2019 | Anand et al. | |
| 2019/0351138 A1 | 11/2019 | Bhandar et al. | |
| 2020/0311432 A1* | 10/2020 | Greiner | G06V 40/10 |
| 2020/0316280 A1 | 10/2020 | Zafiris | |
| 2025/0029716 A1* | 1/2025 | Sossin | G16H 40/40 |

FOREIGN PATENT DOCUMENTS

| | | |
|---|---|---|
| CN | 201727783 U | 2/2011 |
| JP | 2014200415 A | 10/2014 |
| WO | 2021198945 A1 | 10/2021 |

* cited by examiner

*Primary Examiner* — Jacky X Zheng
(74) *Attorney, Agent, or Firm* — Barnes & Thornburg LLP

(57) ABSTRACT

A system for detecting and monitoring lines in a healthcare setting includes a medical device positioned in a healthcare facility. A line extends from the medical device. At least one imaging device is positioned in the healthcare facility to identify the line. A computer determines whether an unwanted condition of the line has occurred.

19 Claims, 7 Drawing Sheets

MEDICAL LINE DETECTION AND MONITORING USING VIDEO

CROSS-REFERENCE TO RELATED APPLICATIONS

This application claims priority under 35 U.S.C. § 119(e) to U.S. Provisional Application No. 63/312,410, filed Feb. 22, 2022, which is expressly incorporated by reference herein.

BACKGROUND

The present disclosure relates to medical lines and, more particularly, to a system and method for medical line detection and monitoring using video.

In critical care, various lines, tubes, and cords can surround a patient. These objects include intravenous lines, percutaneously inserted central catheters, central lines, catheter tubes, endotracheal tubes, extracorporeal membrane oxygenation lines, electroencephalogram lines, electrocardiogram lines, pulse oximeter lines, power cords, and universal serial bus cords. The complexity associated with these lines causes many problems for patient outcomes and caregiver workflow. Challenges related to lines can include unwanted removal of the line. Unwanted removal can be intended by the patient or unintentional from patient movement. The consequences of unwanted removal can include infection, pain or discomfort, or even death. Other challenges can include the line touching the floor or other contaminated objects that can result in infection. Disconnected leads can result in missing vitals data. Additionally, the line can become kinked or severed, especially when line falls below the bedframe and/or becomes tangled. Moreover patient falls can occur as a result of tangled lines or lines on the floor.

In addition to the negative patient outcomes and patient experience, replacing lines is a workflow issue for caregivers who cannot afford to perform additional tasks. Workflow problems are especially challenging when the lines removed require specialists to replace and when the replacement is urgent (e.g. extracorporeal membrane oxygenation lines, endotracheal tubes, etc.).

SUMMARY

The present disclosure includes one or more of the features recited in the appended claims and/or the following features which, alone or in any combination, may comprise patentable subject matter.

According to a first aspect of the disclosed embodiments, a system for detecting and monitoring lines in a healthcare setting includes a medical device positioned in a healthcare facility. A line extends from the medical device. At least one imaging device is positioned in the healthcare facility and separate from the medical device. The at least one imaging device detects the line and identifies the line. A computer device had a processor and executable instructions stored on a non-transitory computer readable medium. The execution of the executable instructions configures the processor to analyze an image of the line from the at least one imaging device to determine whether an unwanted condition of the line has occurred.

In some embodiments of the first aspect, the execution of the executable instructions can configure the processor to segment the image to remove any portions of the image that do not include the line. The processor can trace a path of the line with a curvature analysis algorithm that fits the path to a curve of appropriate order. The processor can determine whether the unwanted condition of the line has occurred based on the curve. The processor can locate a terminus of the line. The processor can identify the unwanted condition of the line if the terminus is located at an unexpected position. The processor can detect a flow rate through the line. The processor can identify the unwanted condition if the flow rate does not match a predetermined flow rate. The processor can activate an alert, if the unwanted condition of the line is detected. The alert can be at least one of a visual alert, audible alert, and vocal alert. The alert can identify the line that has experienced the unwanted condition. The processor can process the image using at least one of convolutional operations, thresholding edge enhancement, and machine learning. The processor can detect the presence of compounds in fluids moving through the line.

Optionally, in the first aspect, the at least one imaging device can include at least one of a video camera, and infrared camera, a depth camera, and a thermal camera. The image of the line can include at least one of a visible image, an infrared image, a depth image, and a thermal image. The at least one imaging device can be mounted on at least one of a wall of the healthcare facility, a ceiling of the healthcare facility, or a fixture in the healthcare facility. The line can include at least one of an intravenous line, a percutaneously inserted central catheter, a central line, a catheter tube, an endotracheal tube, an extracorporeal membrane oxygenation line, an electroencephalogram line, an electrocardiogram line, a pulse oximeter line, a power cord, and a universal serial bus cord. The unwanted condition can include at least one of unwanted removal of the line, a kink in the line, the line touching the floor, disconnection of the line, a severed line, and a tangled line. The line can include a visual indicator that is detected by the at least one imaging device to identify the line. The visual indicator can include a dye flowing through the line. The visual indicator can include at least one of a fiducial marker and grid printed on the line. The visual indicator can include at least one of a barcode, a QR code, or a dot pattern on the line. The visual indicator can be made with at least one of visible ink and infrared ink. The visual indicator can include an optical emitter coupled to generate propagation of light through the line. The optical emitter can be modulated to generate a pattern of illumination that can be read temporally.

According to a second aspect of the disclosed embodiments, a method is performed by a computer device having a processor and executable instructions stored on a non-transitory computer readable medium which, when executed by the processor, causes the computer device to perform the method. The method includes detecting, with an imaging device, a line extending from a medical device positioned in a healthcare facility. The method also includes acquiring, with the imaging device, an image of the line. The method also includes analyzing, with the computer device, the image of the line to determine whether an unwanted condition of the line has occurred.

In some embodiments of the second aspect, the method can also include segmenting, with the computer device, the image to remove any portions of the image that do not include the line. The method can also include tracing, with the computer device, a path of the line with a curvature analysis algorithm that fits the path to a curve of appropriate order. The method can also include determining, with the computer device, whether the unwanted condition of the line has occurred based on the curve. The method can also include locating, with the computer device, a terminus of the line. The method can also include identifying, with the computer device, the unwanted condition of the line if the terminus is located at an unexpected position. The method can also include detecting, with the computer device, a flow rate through the line. The method can also include identifying, with the computer device, the unwanted condition if the flow rate does not match a predetermined flow rate. The method can also include activating an alert, with the computer device, if the unwanted condition of the line is detected. The method can also include processing, with the computer device, the image using at least one of convolutional operations, thresholding edge enhancement, and machine learning. The method can also include detecting, with the computer device, the presence of compounds in fluids moving through the line. The method can also include acquiring, with the imaging device, at least one of a visible image, an infrared image, a depth image, and a thermal image. The method can also include detecting, with an imaging device, a visual indicator on the line. The method can also include dentifying, with the computer device, the line based on the visual indicator. The method can also include injecting a dye into the line to create the visual indicator. The method can also include propagating light, with a light emitter, through the line to create the visual indicator.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
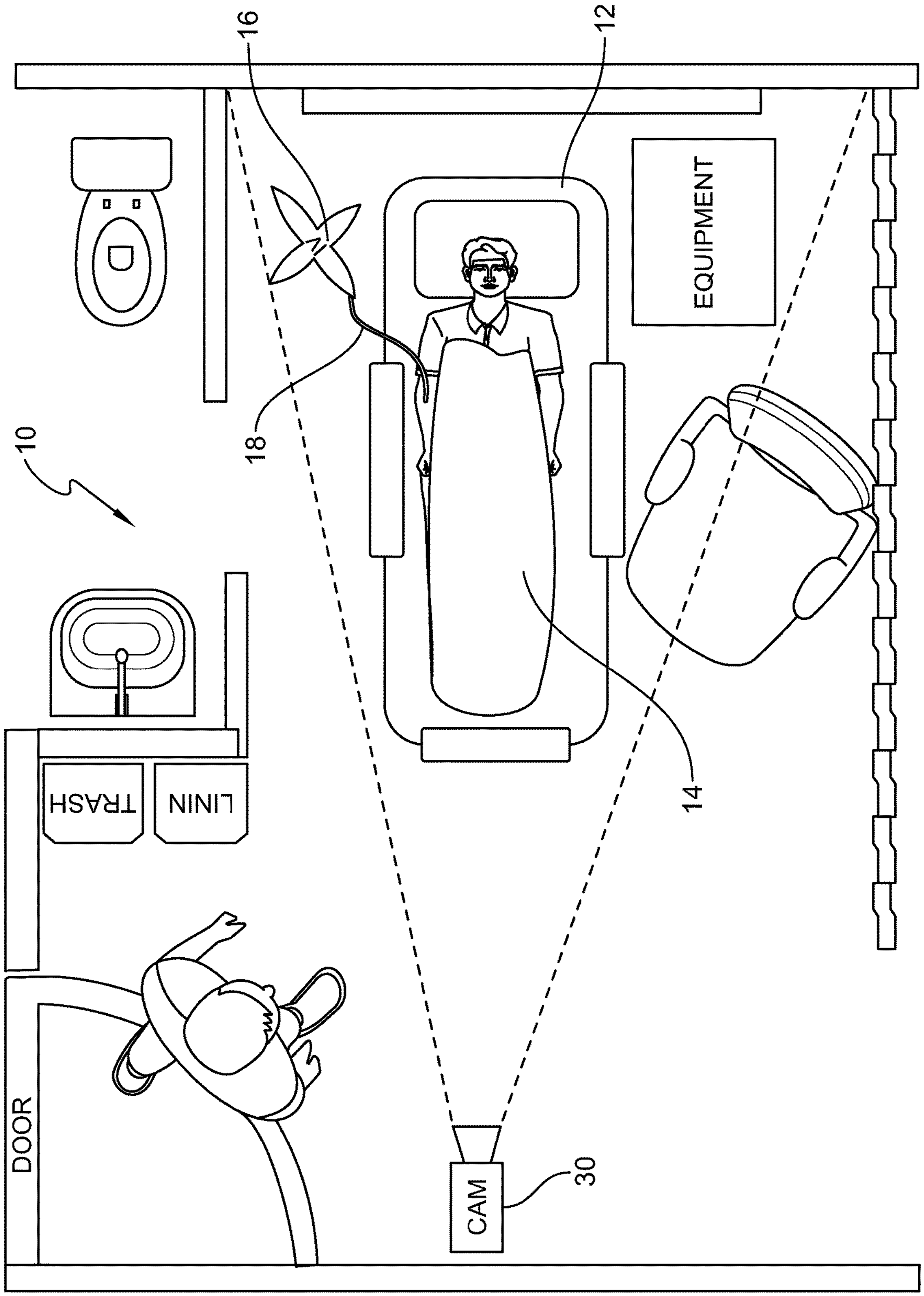
FIG. 1 is a top plan view of a healthcare facility having a patient support apparatus and a medical device, wherein a line extends from the medical device.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIG. 1, a healthcare facility 10 can include a hospital, an urgent care center, a nursing facility, a long-term health facility, or the like. The healthcare facility 10 includes a patient support apparatus 12 that is configured to support a patient 14. The patient support apparatus 12 is illustrated as a patient bed, but can include a chair or any other suitable support surface. At least one medical device 16 is positioned adjacent the patient support apparatus 12. The medical device 16 includes a line 18 extending therefrom. In the illustrated embodiment, the medical device 16 is an intravenous cart carrying an intravenous bag connected to an intravenous line 18. It will be appreciated that the line 18 can also be any one of a percutaneously inserted central catheter, a central line, a catheter tube, an endotracheal tube, an extracorporeal membrane oxygenation line, an electroencephalogram line, an electrocardiogram line, a pulse oximeter line, a power cord, a universal serial bus cord, or the like coupled to a corresponding medical device 16. In some embodiments, the healthcare facility 10 includes a plurality of medical devices 16 and/or a plurality of lines 18.

At least one imaging device 30 is positioned in the healthcare facility 10. The at least one imaging device 30 can be coupled to any one of a wall of the healthcare facility 10, a ceiling of the healthcare facility 10, or a fixture (e.g. furniture, an overhead lift, the at least one medical device 16, etc.) in the healthcare facility 10. The imaging device 30 can have a wide field of view capable of monitoring an entire room of the healthcare facility 10. In some embodiments, the healthcare facility 10 can include any number of imaging devices 30. In some embodiments, a range of the imaging devices 30 can be extended using mirrors. In some embodiments, the imaging device 30 can be any one of a video camera, and infrared camera, a depth camera, a thermal camera, or the like. The imaging device 30 is configured to use image processing techniques to identify the line 18 and monitor for unwanted conditions. The image processing techniques can include the analysis of any one of a visible image, an infrared image, a depth image, a thermal image or the like. The imaging data from the imaging device 30 can be processed using an algorithm that employs traditional image processing techniques (convolutional operations, thresholding, edge enhancement, etc.) in conjunction with machine learning (CNN, etc). The unwanted conditions can include, but are not limited to, unwanted removal of the line 18, a kink in the line 18, the line 18 touching the floor, disconnection of the line 18, a severed line 18, a tangled line 18, occlusion of the line 18, the line 18 looped around an object, the line 18 caught in a side rail of the patient support apparatus 12, the line 18 positioned under the patient 14, the line 18 under tension, and trip hazards, e.g. lines 18 in volumes through which patient legs will move. Unwanted conditions can also include a line 18 that has been removed by someone other than a caregiver, i.e. when a caregiver is not present. Such line 18 removal can be determined using video or a real time locating system. To determine if a line 18 has been pulled out, the change in location of the line 18 relative to the insertion point could be monitored. Furthermore, distortion of bandages or dressings can indicate the line 18 has moved relative to the insertion point.

Figure 2:
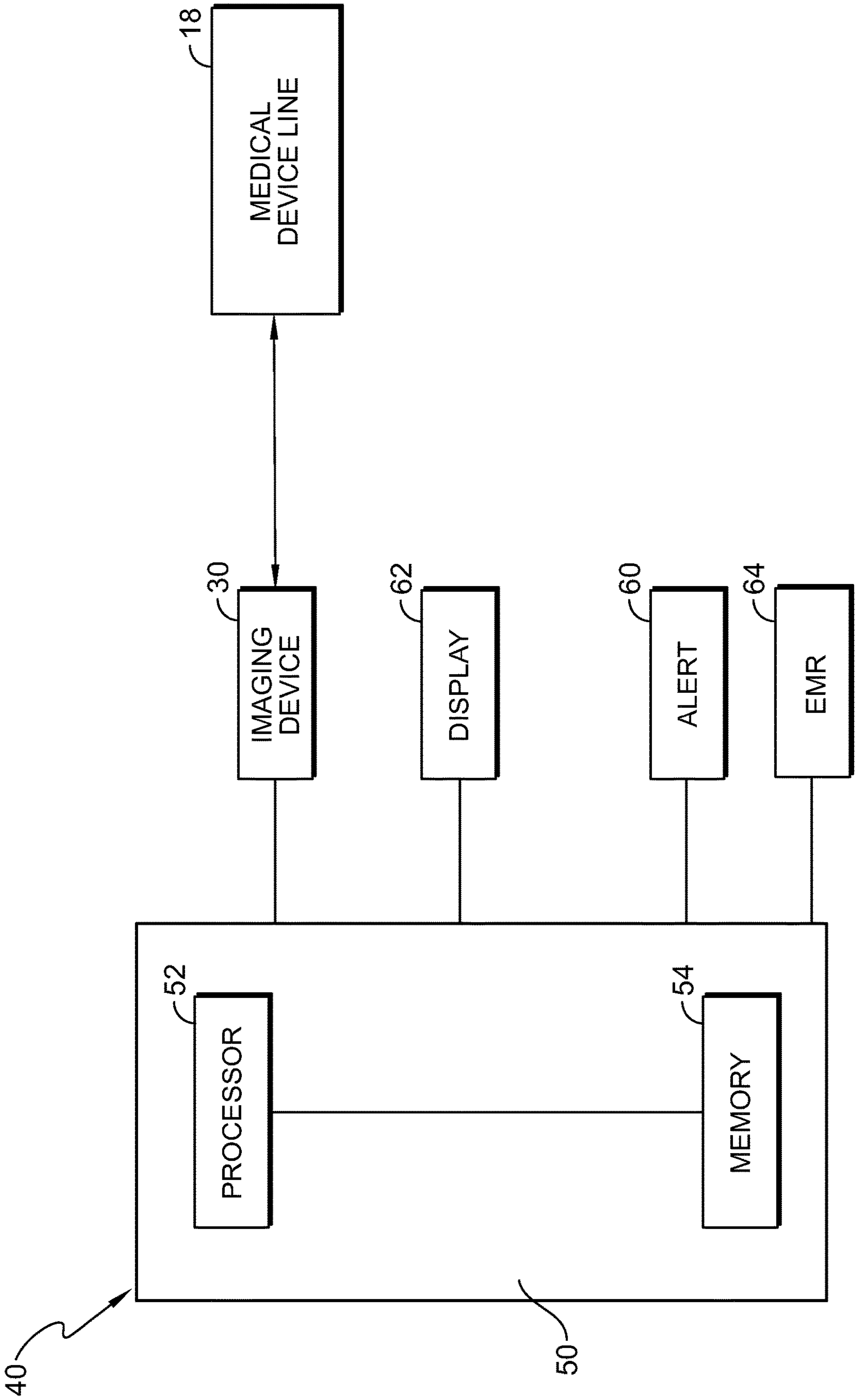
FIG. 2 is a schematic view of control circuitry for detecting and monitoring the shown in FIG. 1.

Referring now to FIG. 2, a system 40 for detecting and monitoring the lines 18 in the healthcare facility 10 includes a computer device 50 having a processor 52 and a memory 54. The memory 54 stores executable instructions on a non-transitory computer readable medium. The executable instructions, when read by the processor 52, cause the processor 52 to analyze an image acquired by the at least one imaging device 30. That is, the imaging device 30 detects a visual indicator (described in more detail below) of the line 18 extending from the medical device 16 and acquires an image of the line 18. The processor 52 analyzes the image of the line 18 to determine whether an unwanted condition of the line 18 has occurred.

An alert 60 is activated if an unwanted condition is detected. The alert 60 can be an audible alert, a visual alert, or vocal alert. In some embodiments, an audible alert can include a sound, whereas a vocal alert can include a digitally recorded message, for example, "patient line occluded." The alert can be conveyed using a wired and/or wireless facility communication system. The alert 60 can be activated in the patient's room of the healthcare facility 10, at a nurse's station (not shown), or at any other location within the healthcare facility 10. In some embodiments, the alert 60 is activated on a mobile device or smart device (not shown) carried by a healthcare worker or family member of the patient. In some embodiments, the patient 14, caregiver, or family member is alerted to unwanted conditions based on permissions set by the caregiver. That is, the alerts can be based on context of patient conditions, medication orders from an electronic medical record (EMR) 64, or encoded information about a medication, wherein the information is encoded in the line 18. The alerts can also be based on pre-selected urgency of different conditions that can be specific to the patient 14 or a unit of the healthcare facility 10. In some embodiments, the alert is delivered to and stored in the electronic medical record 64. For example, the electronic medical record 64 can store each alert created by the system 40. In some embodiments, the alert can communicate a certainty of risk based on calculations by the system 40.

A display 62 can also display information related to the unwanted condition. For example, the display 62 can identify the line 18 in question and provide a summary of the unwanted condition. The display 62 can also provide instructions for correcting or troubleshooting the unwanted condition. The display 62 can be positioned on the patient support apparatus 12. In other embodiments, the display 62 is provided on a remote computer (not shown) located at a nurse's station or other location within the healthcare facility 10. In other embodiments, the display 62 is provided on a mobile device or smart device (not shown) carried by a healthcare worker or family member of the patient.

Figure 3:
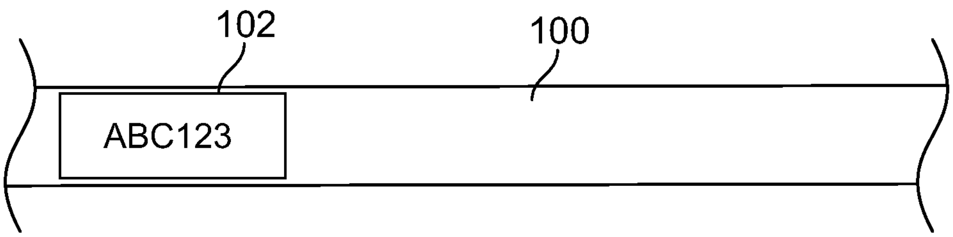
FIG. 3 is a top plan view of an exemplary line having an alpha-numeric code printed thereon.
Figure 4:
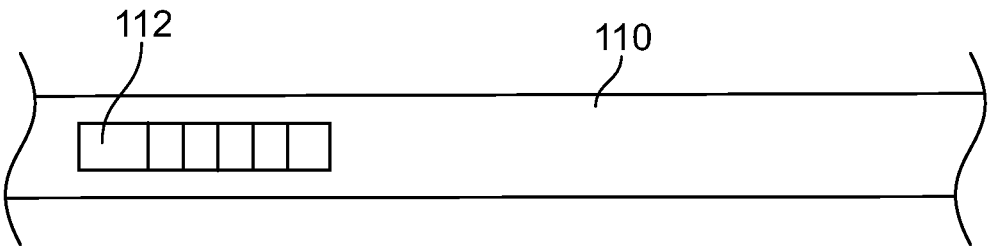
FIG. 4 is a top plan view of an exemplary line having a machine readable code printed thereon.
Figure 5:
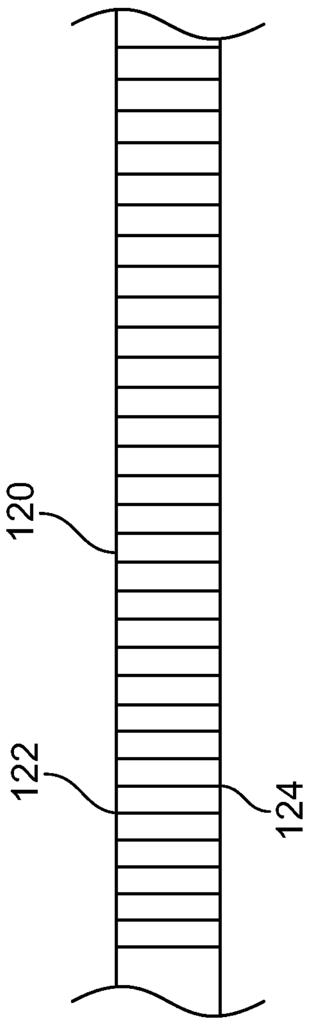
FIG. 5 is a top plan view of an exemplary line having a pattern printed thereon.

Various visual indicators can be used to identify the line 18. FIG. 3 illustrates a line 100 having an alpha-numeric code 102 printed thereon. The alpha-numeric code 102 includes a series of numbers and letters that identify the line 100. For example, an intravenous line can have a specific alpha-numeric code 102 associated therewith. Likewise, a central line can have a different alpha-numeric code 102. FIG. 4 illustrates a line 110 having a machine readable code 112 printed thereon. The machine readable code can include a barcode or QR code that identifies the line 110. For example, an intravenous line can have a specific machine readable code 112 associated therewith. Likewise, a central line can have a different machine readable code 112. FIG. 5 illustrates a line 120 having a pattern 122 printed thereon. The pattern 122 can include a series of lines, a series of dots, fiducial markers, grids, point clouds, or other patterns that identify the line 120. For example, an intravenous line can have a specific pattern 122 associated therewith. Likewise, a central line can have a different pattern 122. In some embodiments, changes in the pattern 122 can indicate an unwanted condition. For example, FIG. 5 illustrates a series of parallel marks 124. If an angle between adjacent marks 124 exceeds a predetermined value, the system 40 can determine that the line 120 is kinked. Moreover, the marks 124 can include numeral markers indicating a length of the line 120. Accordingly, the marks 124 can indicate the length of line 120 behind an obstruction. For example, if a portion of the line 120 is positioned under a sheet, the system 40 can determine how much of the line 120 is under the sheet based on the numeral markers.

The visual indicators of FIGS. 3-5 can be printed with visible ink or infrared ink. In the case of infrared ink, the imaging device 30 provided in the system 40 includes an infrared camera capable of detecting the infrared ink. In some embodiments, visual indicators are also printed on dressings and bandages. For example, a visual indicator for an intravenous line can also be printed on the dressing at the insertion point of the intravenous line. Accordingly, the system 40, upon identifying the intravenous line can detect that the line is still present at the intended insertion point. In some embodiments, the visual indicator is encoded with information related to medication within the line 18.

Figure 6:
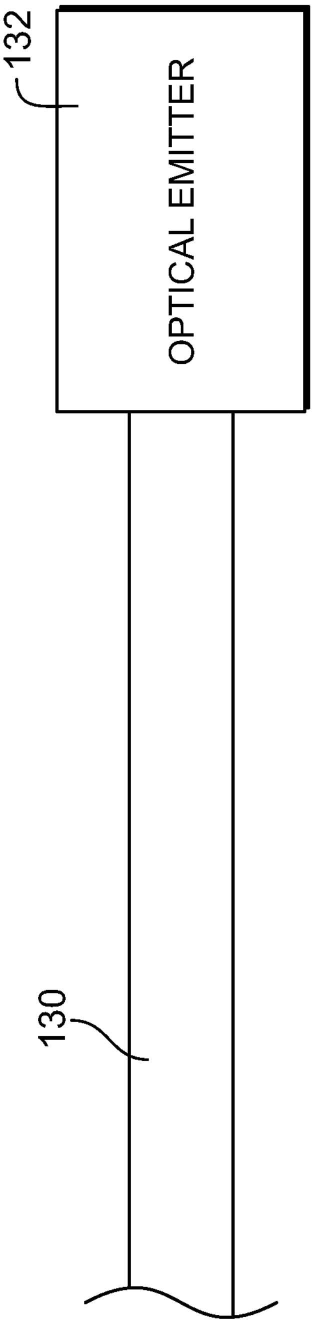
FIG. 6 is a top plan view of an exemplary line having an optical emitter.

FIG. 6 illustrates an exemplary line 130 having an optical emitter 132 that couples to the line 130 such that propagation of light through the line 130 takes advantage of an aspect ratio (long and thin) of the line 130 and the total internal reflection of the material of the line 130 (similar to fiber optics). In some embodiments, the optical emitter 132 can be a light emitting diode. The optical emitter 132 can be modulated such that a known pattern of illumination can be read temporally by the imaging device 30. At the terminus of the line 130 (patient side) the dispersion of the light presents a significant characteristic artifact in the image acquired by the imaging device 30 that can be detected and extracted. Instruments not wanting to be modified to include the optical emitter 132 could be bypassed with a battery powered clip on device that achieves the same as above. An advantage of the modulated light emission is that additional data can be encoded and communicated. For example, the modulation could communicate that the line 130 is an intravenous line, the flow rate of the line 130, and the medication being administered. This information could help the system 40 to determine the urgency of issuing an alert if there is an unwanted condition detected with the line 130. In some embodiments, the light emission through the line 130 can assist in detecting presence of compounds in fluids moving through line 130.

Figure 7:
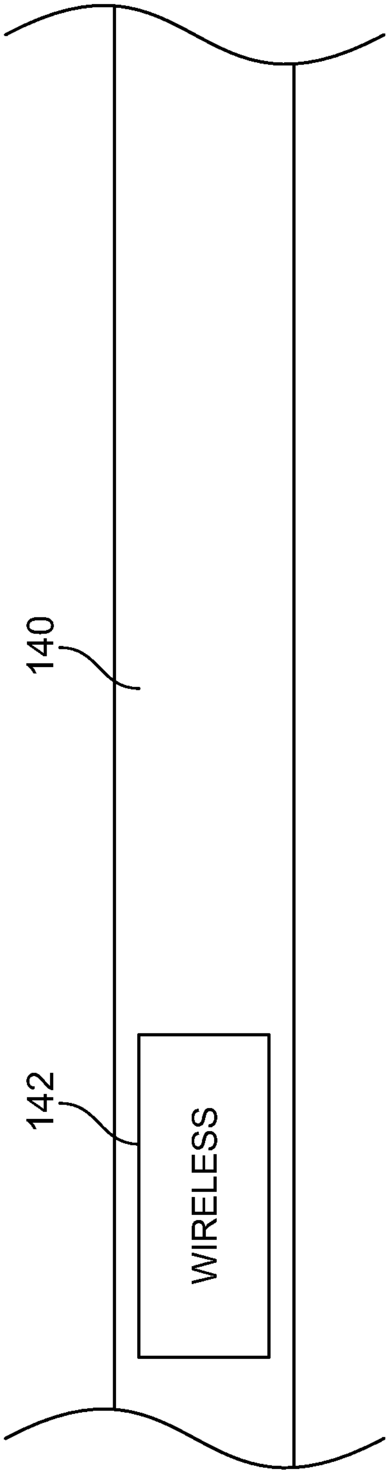
FIG. 7 is a top plan view of an exemplary line having wireless communication tags.

Referring now to FIG. 7, a line 140 can be equipped with wireless communication tags 142. The wireless communication tags 142 can include near field communication tags, radio frequency identification tags, or the like. The system 40 can include devices to communicate with the wireless communication tags 142 to identify the line 140. For example, an intravenous line can have a specific wireless communication tag 142 associated therewith. Likewise, a central line can have a different wireless communication tag 142.

In some embodiments, the line 18 is doped with a dye. That is, dye is mixed with the fluid flowing through the line 18. As such, the imaging device 30 detects the dye to identify the line 18. In some embodiments, the color of the dye identifies the line 18. For example, a line 18 carrying a first medication can have a specific color associated therewith. Likewise, a line 18 carrying a second medication can have a different color associated therewith. It will be appreciated, that, if the dye is not detected by the imaging device 30, the lack of detection can indicate a blockage in the line 18.

In one embodiment, the system 40 is pre-programmed to detect specific lines 18. For example, the system 40 can be pre-programmed to associate a particular bar code with an intravenous line. Likewise, the system 40 can be pre-programmed to associate a particular dot pattern with a central line. As such, all the intravenous lines within the healthcare facility 10 are marked with the same bar code, and all the central lines within the healthcare facility are marked with the same dot pattern. Accordingly, regardless of the room in which the system 40 is operating, the system 40 is pre-programmed to identify the intravenous line and the central line. The shape of the line 18 or location of the line 18 relative to other objects could further be identified based on patterns printed on the lines 18. The patterns could be printed on the lines 18 by manufacturers, in an aftermarket printing process by hospitals, or by caregivers themselves by adhering stickers onto lines 18. The patterns could be as simple as a repeating barcode, or a more complicated grid of points that can indicate length (like a meter stick). Further identification could be integrated into the bandages, dressings, or other adhesives that clinicians already use to secure lines 18.

In another embodiment, the caregiver trains the system 40 to identify the lines 18. For example, upon set up of the room, the caregiver can lift the intravenous line so that the visual indicator on the intravenous line is visible by the system 40. The system 40 is then programmed to associate the visual indicator on the intravenous line with the intravenous line. The caregiver can program the system 40 using auditory commands and/or by entering information into a control panel. At this time, the system 40 can instruct the caregiver on proper placement of a nominal position of the intravenous line. Additionally, the system 40 using the methods described below can trace the intravenous line to associate a particular position of the line 18 with the intravenous line. As the caregiver identifies the lines 18 and programs the system 40, the system 40 can utilize machine learning to map the placement of lines 18 throughout the room of the healthcare facility 10. In another embodiment, detecting and monitoring of the lines 18 is fully automated entirely by algorithms that detect the lines 18, the relationship and orientation of the line 18 to the patient 14, and unwanted conditions.

Figure 8:
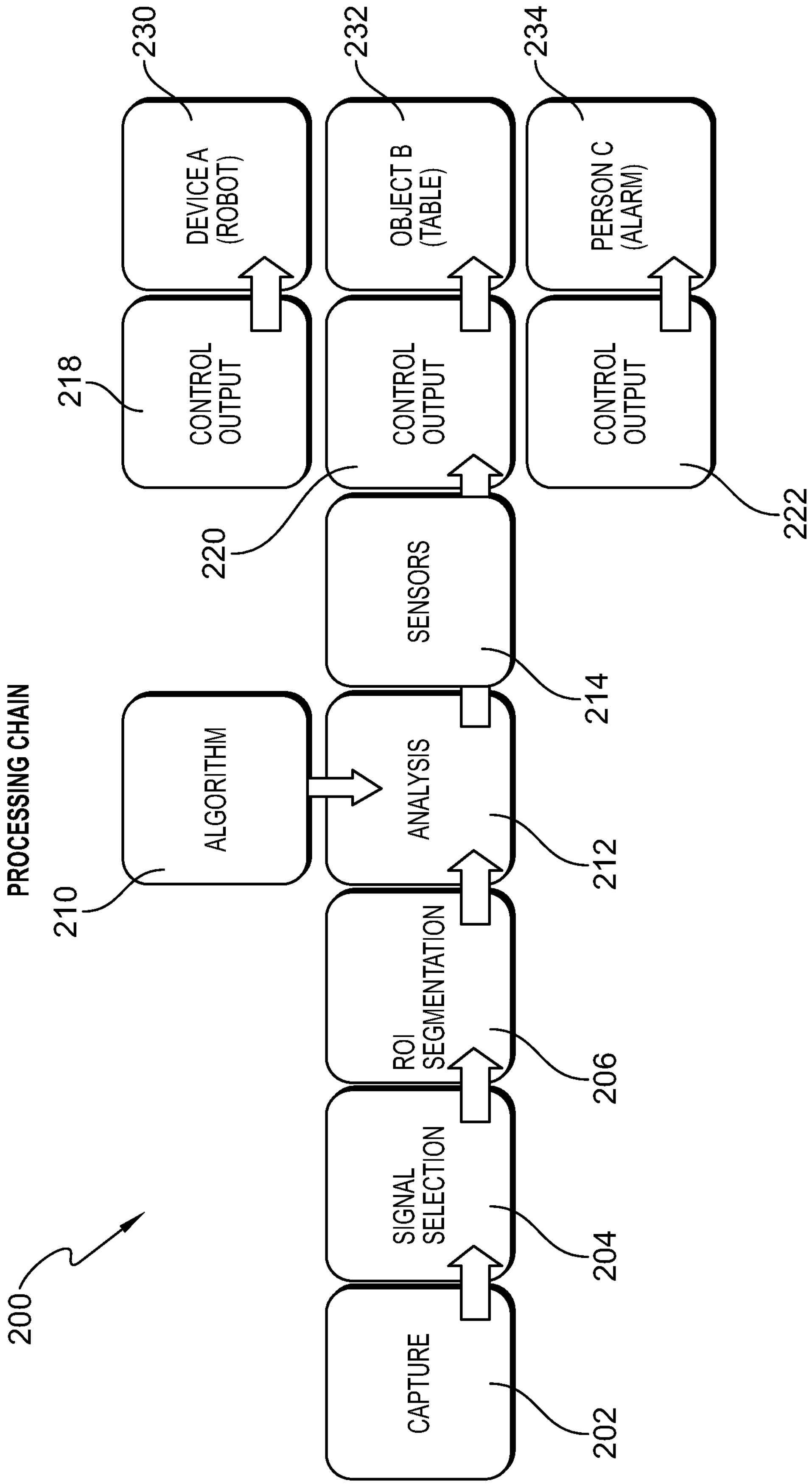
FIG. 8 is a flowchart for a process for segmenting an image from the imaging device shown in FIG. 1.

FIG. 8 illustrates a flowchart 200 for a process for segmenting an image from the imaging device 30. At block 202, an image of the healthcare facility 10 is captured. In some embodiments, a plurality of images are captured. The images can be any combination of visible images, infrared images, depth images, thermal images or the like. At block 204, the system 40 selects a signal. The signal selection acts as a filter of the raw modality inputs. Each captured image and/or frame is analyzed for a visual quality of the presentation of the line. In one embodiment, the system 40 uses color segmentation or thresholding to sum the total number of pixels that present as a predefined color in a color image such that a color/hue presentation is just that of the color of the line 18. If the sum is above a threshold then that image frame is passed down the processing chain. In another embodiment, the medical device 16 is detected within the frame by employing a trained CNN or Haar cascade filter designed to detect those objects. At block 206, the image is segmented into regions of interest.

An algorithm is applied to the image at block 210. In particular, a rule set is modeled in the algorithm. The algorithm "know-how" is codified by creating a multidimensional graph of the lines 18, medical devices 16, and the patient 14. For each item various objects are defined to capture the operational and physical envelope of the item. The objects can be grouped, nested, or linked. For example, presentation characteristics can include dimensions, color, weight, length, etc. States of the items can be defined, wherein the states can include open, closed, sterile, stationary, moving, idle, locked, crossed, tangled, kinked, stretched, snagged, etc. Additionally transitions of the items can be defined. For example, a line 18 can transition from safe to unsafe, or a line 18 can transition from sterile to used; etc. Inputs and outputs can also be defined, for example alarms, operational inputs/outputs, pump infusing inputs/outputs, pump idle inputs/outputs, control panel inputs/outputs, and illumination inputs/outputs.

An analysis takes place at block 212 to identify the lines 18. The lines 18 can be identified using classical deterministic image processing algorithms. For example, convolutional operations to detect edges and textures can be used to process a raw image into a set of masks and blobs. Optionally, an atlas based representation tree is applied for the determination of an object within the frame. This tree shows dependence information about where a line 18 should be with respect to another object and allows the algorithm to concentrate and provide threshold acceptance of identification of the object. For example is the patient 14 is imaged near the line 18, the line 18 is determined to be attached. If the image only includes the line 18, the line 18 is determined to have a loose fit.

The lines 18 can also be identified using a machine learning algorithm, wherein a model is selected for each appropriate object from a zoo of pre-trained models and confidence intervals are set for an appropriate threshold. The machine learning then returns information about the locality of the known objects.

Lines 18 that are identified are then localized within the three-dimensional space of the room of the healthcare facility 10. Using a photogrammetry approach with information known about the size and length of the line 18 an estimation of the location of the line 18 can be computed. Using a source modality like time of flight data, the position of the line 18 can be directly observed once the line 18 is located within the field of view as a lookup into the three-dimensional point cloud data. Additionally, the presentation of the line 18 is given a set of orientation vectors with respect to a global coordinate system.

At block 214 sensors are applied. As used herein the sensors are a classifier of a logical set of states or transitions that an object experiences to create a Boolean trigger that can be used to enable or select protocols, control the environment, or alert an external system. The sensors can directly observe events (an object moved), infer events (a patient transfer position implies that the patient turned over) or predictive events (a line 18 is applied so the patient is at risk). At blocks 218, 220, and 222, control outputs are provided to various objects 230, 232, and 234. It will be appreciated that any number of control outputs can be provided to any number of objects.

In some embodiments, a training mode occurs where the caregiver trains the system by identifying the lines 18. To start the training, the caregiver can press a button on the imaging device 30 or the patient support apparatus 12. Training can also be initiated through a mobile device application or by a verbal command that is heard through the imaging device 30, the patient support apparatus 12, a phone, or a nurse call. For example, the caregiver could say "[listening word] identify lines," where the [listening word] is a trigger for the system 40. Alternatively, the system 40 can initiate training by instructing "please identify lines."

During the training mode, the system 40 can name lines 18 that the caregiver then touches in sequence, or the caregiver can name lines 18 while touching them. The system 40 then uses the identified locations as a seed three-dimensional position to the algorithm.

Figure 9:
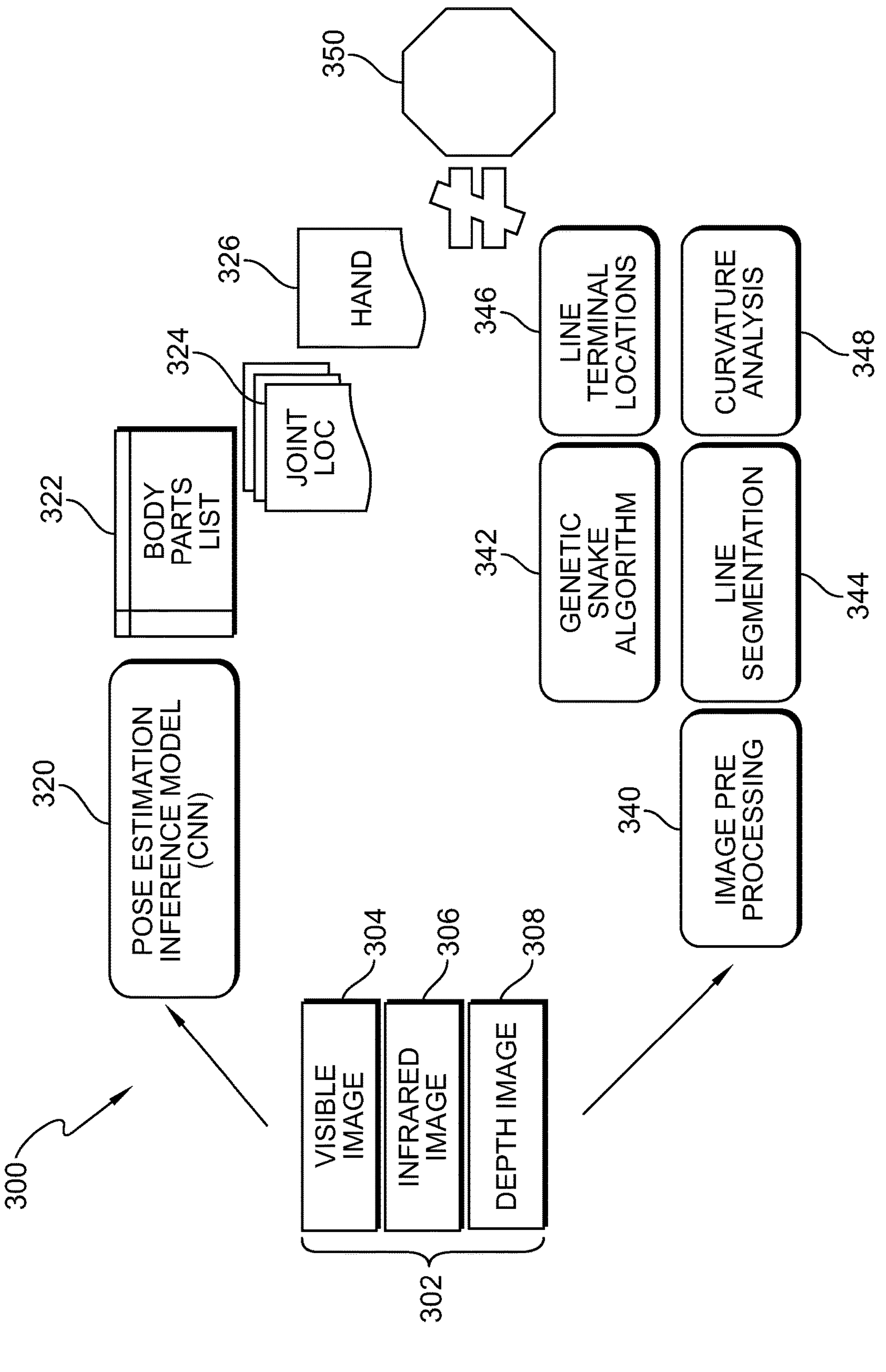
FIG. 9 is a flowchart for a method for detecting and monitoring the line shown in FIG. 1.

FIG. 9 illustrates a flowchart 300 for a method for detecting and monitoring a line 18. The processing algorithm uses both conventional and machine learning techniques simultaneously combined to detect hazards. At block 302, the system 40 acquires at least one of a visible image 304, an infrared image 306, and a depth image 308. In some embodiments, a thermal image can also be acquired. Pose estimation occurs at block 320 and generates a list of three-dimensional space positions that correspond to a physical presentation of the patient 14 in the patient support apparatus 12. These positions are extracted to generate a skeleton, at block 322. The skeleton is then searched for a region of interest (e.g. for a central pic line at the hand, the region of interest is the wrist) that corresponds to a location where the line 18 should be located, at block 324. The region of interest is parsed to produce a single three-dimensional space position, at block 326.

Simultaneously, the raw images from block 302 are fed to an image processing sequence that segments out each portion of the image that is not easilly identified as a line 18, at block 340. At block 342, a genetic snake algorithm is employed to trace the line 18. Any random location on the line 18 is selected and traversed with the snake following the line 18 in both directions, at block 344. When the snake hits an obstruction (from an occlusion or artifact) an elastic dead reckoning algorithm uses the current trajectory of where the snake has been to allow the snake to hop over the obstruction in the two-dimensional image. The distance the snake is allowed to traverse (elasticity) is set a priori. If the snake is unable to find a landing spot within that distance, the current point is marked as a terminus, at block 346.

Post processing of the snakes' path is sent to a curvature analysis algorithm, at block 348, that fits the path to a curve of appropriate order. If no fit can be made for each segment of the snake path, the line 18 is found to be taught or stretched and represents a hazard, at block 350. If the terminus of the snake is not located at the expected position for the line 18 (e.g., an IV at the hand), a hazard is also detected, at block 350. When negative conditions are detected, the system 40 alerts caregivers and patients as appropriate. Based on patient and/or family cognitive ability and medical literacy, caregivers can opt to have line issues communicated by a mobile device application or by the patient support apparatus speakers. Regardless of patient or family involvement, potential issues could be communicated to caregivers and escalated using typical alert management. For issues that are lower priority (e.g. a tangled saline drip) a notification could be delayed until a caregiver is in the room as detected by the imaging device 30 or a real time locating system.

When a negative condition is detected, the system 40 can also draw attention by having a projector or other light highlight the location of the condition in question (e.g., if a line is touching the floor or caught in a siderail). Although sheets and other visual obstructions could limit some of the ability of the system 40 to detect certain conditions, some methods allow the system 40 to detect negative outcomes even when obstructed. For example, if the system has visibility to the line at its source and/or destination. In this case, knowledge about the state of the line (it is continuous) would allow the system to make assumptions about its routing (under covers, or other obstructions). Given that standards set the length of lines by their use and class, the system 40 has knowledge a-priori about all the routes the line could possibly take where it is occluded. This is a computational matrix that could be generated in real time. Assuming the system 40 can see the line 18 at the time it is inserted into the patient, the system 40 can recognize points on the line 18 and determine the relative lengths of different points relative to the end of the line 18. If the system later sees points removed from the sheets that allow it to determine the known length of the line 18 under a sheet is shorter than the distance of the end of the line 18 to the visible part of the line 18, then it can be concluded a line 18 has been pulled. Similarly, if the length of line 18 under the sheet is determined to be very long, then there is an increased chance of tangling or entanglement with the patient or other objects. If a line 18 becomes undiscernible the system 40 can use a hysteresis-based rule parser to determine if the condition warrants an alarm. For example, a pic line that was detected becomes no longer visible. No potential hazards were observed within a radius prior to loss of lock (the rail is down, there is no tray or cell phone present). The algorithm returns a safe condition.

Video can allow for detecting additional information about the operation of the lines 18. For example, with sufficient resolution, the system 40 can detect the flow rate of fluids. The actual flow rate could be compared to the patient conditions or medication orders (if the system 40 is connected to the electronic medical record 64) to detect possible dosing errors and alert accordingly. Similarly, the system could use color and/or infrared to determine the presence of certain compounds in blood or urine. Certain findings relative to specific patient conditions (using the electronic medical record 64) could flag potential complications that could be alerted to caregivers.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used, the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations can be apparent to those skilled in the art. Also, while multiple inventive aspects and principles have been presented, they need not be utilized in combination, and many combinations of aspects and principles are possible in light of the various embodiments provided above.

The invention claimed is:

1. A system for detecting and monitoring lines in a healthcare setting, the system comprising:
   a medical device positioned in a healthcare facility,
   a line extending from the medical device,
   at least one imaging device positioned in the healthcare facility and separate from the medical device, wherein the at least one imaging device detects the line and identifies the line, and
   a computer device having a processor and executable instructions stored on a non- transitory computer readable medium, wherein the execution of the executable instructions configures the processor to;
   analyze an image of the line from the at least one imaging device to determine whether an unwanted condition of the line has occurred,
   segment the image to remove any portions of the image that do not include the line,
   trace a path of the line with a curvature analysis algorithm that fits the path to a curve of appropriate order, and
   determine whether the unwanted condition of the line has occurred based on the curve.

2. The system of claim 1, wherein the execution of the executable instructions configures the processor to:
   locate a terminus of the line, and
   identify the unwanted condition of the line if the terminus is located at an unexpected position.

3. The system of claim 1, wherein the execution of the executable instructions configures the processor to:
   detect a flow rate through the line, and
   identify the unwanted condition if the flow rate does not match a predetermined flow rate.

4. The system of claim 1, further comprising an alert, wherein the execution of the executable instructions configures the processor to activate the alert, if the unwanted condition of the line is detected.

5. The system of claim 4, wherein the alert is at least one of a visual alert, audible alert, and vocal alert.

6. The system of claim 4, wherein the alert identifies the line that has experienced the unwanted condition.

7. The system of claim 1, wherein the execution of the executable instructions configures the processor to process the image using at least one of convolutional operations, thresholding edge enhancement, and machine learning.

8. The system of claim 1, wherein the execution of the executable instructions configures the processor to detect the presence of compounds in fluids moving through the line.

9. The system of claim 1, wherein the at least one imaging device includes at least one of a video camera, and infrared camera, a depth camera, and a thermal camera.

10. The system of claim 9, wherein the image of the line includes at least one of a visible image, an infrared image, a depth image, and a thermal image.

11. The system of claim 1, wherein the at least one imaging device is mounted on at least one of a wall of the healthcare facility, a ceiling of the healthcare facility, or a fixture in the healthcare facility.

12. The system of claim 1, wherein the line includes at least one of an intravenous line, a percutaneously inserted central catheter, a central line, a catheter tube, an endotracheal tube, an extracorporeal membrane oxygenation line, an electroencephalogram line, an electrocardiogram line, a pulse oximeter line, a power cord, and a universal serial bus cord.

13. The system of claim 1, wherein the line includes a visual indicator that is detected by the at least one imaging device to identify the line.

14. The system of claim 13, wherein the visual indicator includes a dye flowing through the line.

15. The system of claim 13, wherein the visual indicator includes at least one of a fiducial marker, a grid, a barcode, a QR code, or a dot pattern on the line.

16. The system of claim 13, wherein the visual indicator is made with at least one of visible ink and infrared ink.

17. The system of claim 13, wherein the visual indicator includes an optical emitter coupled to generate propagation of light through the line.

18. The system of claim 17, wherein the optical emitter is modulated to generate a pattern of illumination that can be read temporally.

19. A system for detecting and monitoring lines in a healthcare setting, the system comprising:
   a medical device positioned in a healthcare facility,
   a line extending from the medical device,
   at least one imaging device positioned in the healthcare facility and separate from the medical device, wherein the at least one imaging device detects the line and identifies the line, and
   a computer device having a processor and executable instructions stored on a non- transitory computer readable medium, wherein the execution of the executable instructions configures the processor to analyze an image of the line from the at least one imaging device to determine whether an unwanted condition of the line has occurred,
   wherein the unwanted condition includes at least one of unwanted removal of the line, a kink in the line, the line touching the floor, disconnection of the line, a severed line, and a tangled line.

* * * * *